(12) United States Patent
Salsbury, Jr. et al.

(10) Patent No.: US 8,486,957 B2
(45) Date of Patent: Jul. 16, 2013

(54) CHEMOTHERAPEUTIC FOR INDUCING AN MSH2-DEPENDENT APOPTOTIC PATHWAY

(75) Inventors: Freddie R. Salsbury, Jr., Winston-Salem, NC (US); Karin D. Scarpinato, Clemmons, NC (US); S. Bruce King, Walnut Cove, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 347 days.

(21) Appl. No.: 12/711,306

(22) Filed: Feb. 24, 2010

(65) Prior Publication Data

US 2010/0239522 A1    Sep. 23, 2010

Related U.S. Application Data

(63) Continuation-in-part of application No. PCT/US2008/009979, filed on Aug. 22, 2008.

(60) Provisional application No. 60/957,761, filed on Aug. 24, 2007.

(51) Int. Cl.
- *A61K 31/475* (2006.01)
- *A61K 41/00* (2006.01)
- *A61K 31/44* (2006.01)
- *A61K 45/06* (2006.01)
- *C07D 471/14* (2006.01)

(52) U.S. Cl.
USPC .............. 514/280; 514/283; 514/34; 514/43; 514/49; 546/53

(58) Field of Classification Search
USPC ............ 514/280, 283, 34, 43, 49, 83; 546/53
See application file for complete search history.

(56) References Cited

U.S. PATENT DOCUMENTS

2006/0009506 A1 * 1/2006 Westwick et al. ............. 514/395
2006/0264384 A1 * 11/2006 Johansen et al. ................ 514/27

OTHER PUBLICATIONS

Meyer, J, Pharmacokinetics and Biopharmaceutics, 24, pp. 449-459, 1996.*
Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
Pearce et al. (Proc Natl. Acad. Sci. 86, 5128-32, Jul. 1989).*
Waikar et al. (Br. J. Pharmacology, 1994, 111, 213-218).*
Brent J et al. Fomepizole for the treatment of methanol poisoning. The New England Journal of Medicine. Feb. 8, 2001; 344(6): 424-429.
Tephly TR. The toxicity of methanol. Life Sciences. 1991; 48(11): 1031-1041.

* cited by examiner

*Primary Examiner* — Sreeni Padmanabhan
*Assistant Examiner* — Uma Ramachandran
(74) *Attorney, Agent, or Firm* — Myers Bigel Sibley & Sajovec, P.A.

(57) ABSTRACT

A method of treating cancer in a subject in need thereof comprises administering said subject reserpine, yohimbine, an analog thereof, or a pharmaceutically acceptable salt or prodrug thereof, in an amount effective to treat the cancer. Compounds and compositions useful for carrying out the method are also described.

5 Claims, 7 Drawing Sheets

MTS assay of MSH2-proficient and –deficient cells (HEC59 and HEC59 chr.2) after the exposure to increasing amounts of Reserpine (24h).

CHEMOTHERAPEUTIC FOR INDUCING AN MSH2-DEPENDENT APOPTOTIC PATHWAY

RELATED APPLICATIONS

This application claims priority to under 35 U.S.C. §120, and is a continuation-in-part of, PCT application no. PCT/US2008/009979, filed Aug. 22, 2008, which claims the benefit under 35 U.S.C. §119(e) of U.S. Provisional Patent Application Ser. No. 60/957,761, filed Aug. 24, 2007, the disclosure of each of which is incorporated herein by reference in its entirety.

STATEMENT OF GOVERNMENT SUPPORT

This invention was made with Government support under Grant No. RO1 CA101829 from the NIH. The US Government has certain rights to this invention.

FIELD OF THE INVENTION

The present invention concerns methods and compositions for the treatment of cancer.

BACKGROUND OF THE INVENTION

The p53 gene is one of the most studied and well-known genes. p53 plays a key role in cellular stress response mechanisms by converting a variety of different stimuli, for example, DNA damage, deregulation of transcription or replication, and oncogene transformation, into cell growth arrest or apoptosis. However, loss of p53 activity in tumors is associated with faster tumor progression and resistance to cancer treatment. See, e.g., U.S. Pat. No. 6,593,353; see also U.S. Pat. Nos. 6,998,117; 6,017,524; 5,908,750; and 5,744,310.; M. Greenblatt et al., *Cancer Res.* 54, 4855-4878 (1994). Hence, there is a need for new ways to treat cancers in which p53 deficiency is found.

SUMMARY OF THE INVENTION

There is an unmet need for treating cancers in which p53 deficiency is found. One such p53 independent mechanism has recently been identified in mismatch repair proteins. Historically, mismatch repair proteins have been identified in recognizing and processing replication errors in the DNA. In addition to the recognition of mismatches, bacterial MutS protein and its eukaryotic homolog also recognize certain DNA damage. In response to such DNA damage, mismatch repair proteins activate cell death rather than damage repair. This cell death pathway is essentially p53 independent. Using a combination of computational modeling and cell biology, we have identified a "death conformation" of the MutS homologous proteins that trigger the cell death pathway. We then identified compounds, as well as the structural requirements for proposed compounds, that would fit into the "death conformation" and therefore initiate cell death in the absence of DNA. Since this cell death mechanism is p53-independent, the proposed compounds can be effective for the treatment of p53-deficient tumors.

Accordingly, a first aspect of the invention is a method of treating cancer in a subject in need thereof, comprising administering said subject an active compound as described herein in an amount effective to treat said cancer.

A second aspect of the present invention is a composition comprising an active agent as described herein in a pharmaceutically acceptable carrier. The composition optionally includes at least one additional chemotherapeutic agent.

A further aspect of the present invention is the use of an active compound as described above for the preparation of a medicament for the treatment of cancer as described herein.

Reserpine has been suggested in conjunction with the treatment of prostate cancer (see U.S. Pat. No. 6,635,648 to Adams et al.), but has neither been suggested nor described for the treatment of p53-deficient cancers.

The present invention is explained in greater detail in the drawings herein and the specification set forth below. The disclosures of all United States patent references cited herein are to be incorporated herein by reference in their entirety.

DETAILED DESCRIPTION OF EMBODIMENTS OF THE INVENTION

Figure 1:
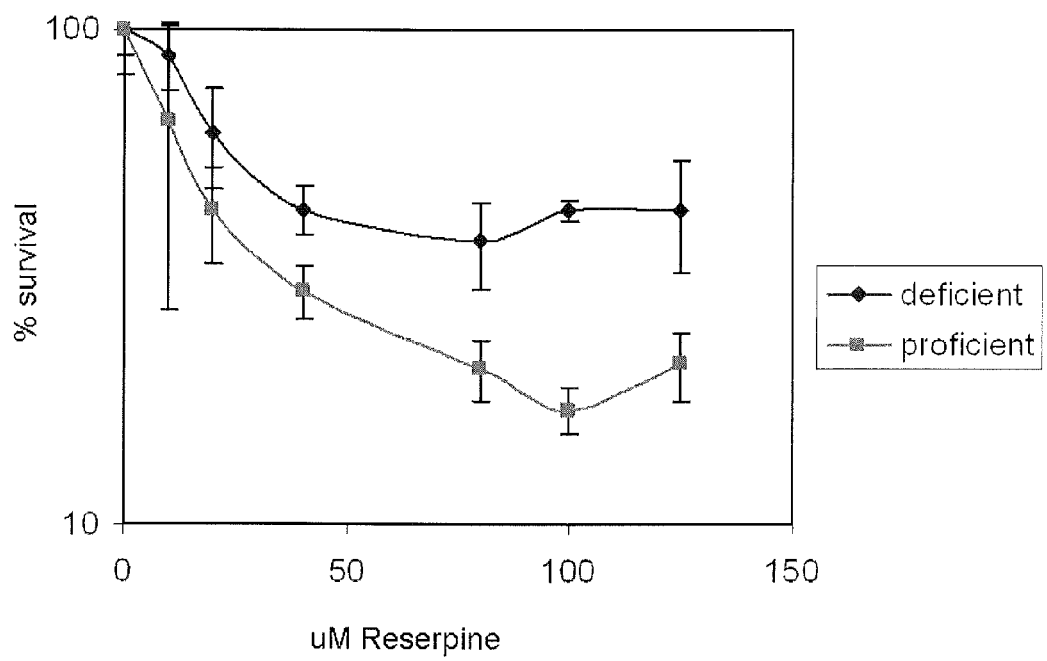
FIG. 1. MTS assay of MSH2-proficient and -deficient cells (HEC59 and HEC59 chr.2) after the exposure to increasing amounts of Reserpine (24h).

"Cancer" as used herein is particularly concerned with p53 deficient tumors or cancers; or those in which p53 deficiency is found. Such cancers are known and described in, for example, U.S. Pat. Nos. 6,593,353; 6,998,117; 6,017,524; 5,908,750; and 5,744,310; and in M. Greenblatt et al., *Cancer Res.* 54, 4855-4878 (1994). It will be appreciated that, in some cases, cancers or tumors of a particular type can be treated by the method of the present invention even though those particular tumors are not p53 deficient. Hence, examples of cancers that can be treated by the methods of the present invention include, but are not limited to, prostate cancer, lung cancer, colon cancer or colorectal cancer, esophageal cancer, ovarian cancer, skin cancer, and gastric cancer. In some embodiments, the cancer is a platinum-resistant cancer, such as a cisplatin (cisplatinum) or oxaliplatin resistant cancer.

"Treat" as used herein refers to any type of treatment that imparts a benefit to a patient afflicted with a disease, including improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Prodrug" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound or active agent, for example, by hydrolysis in blood.

"Loweralkyl" as used herein alone or as part of another group, refers to a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, and the like. The term "loweralkyl" is intended to include both substituted and unsubstituted alkyl or loweralkyl unless otherwise indicated and these groups may be substituted with from 1 to 4 groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocylooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Loweralkenyl" as used herein alone or as part of another group, refers to a straight or branched chain hydrocarbon containing from 1 to 4 carbon atoms which include 1 to 2 double bonds in the normal chain Representative examples of alkenyl include, but are not limited to, vinyl, 2-propenyl, 3-butenyl, 2-butenyl, and the like. The term loweralkenyl" is intended to include both substituted and unsubstituted alkenyl or loweralkenyl unless otherwise indicated and these groups may be substituted with groups as described in connection with loweralkyl above.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, benzopyran, benzopyran-2-one, benzopyran-4-one, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above, particularly aryl such as phenyl, naphthyl, benzopyran, benzopyran-2-one, and benzopyran-4-one, optionally substituted from 1 to 3 times with independently selected loweralkoxy, hydroxy, or carboxy.

"Arylalkyl" and "arylalkynyl" as used herein alone or as part of another group, refers to an aryl group, as defined herein, appended to the parent molecular moiety through an alkyl or alkenyl group, as defined herein. Representative examples of arylalkyl include, but are not limited to, benzyl, 2-phenylethyl, 3-phenylpropyl, 2-naphth-2-ylethyl, and the like.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

The present invention is primarily concerned with the treatment of human subjects (including both male and female subjects; and including infant, juvenile, adolescent, adult, and geriatric subjects), but the invention may also be carried out on animal subjects, particularly mammalian subjects such as mice, rats, dogs, cats, livestock and horses for veterinary purposes, and for drug screening and drug development purposes.

1. Active Compounds.

Active compounds of the present invention include yohimbine, reserpine, and analogs thereof, including but not limited to compounds of Formula Ia:

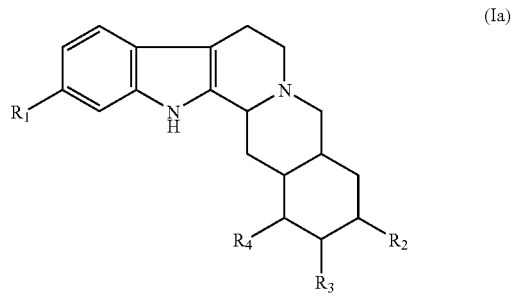

(Ia)

wherein:

$R_1$ is H, loweralkyl, or loweralkoxy, preferably H or methoxy; most preferably methoxy;

$R_2$ is H, hydroxy, or —OC(O)R, where R is aryl (e.g., naphthyl, benzopyran, benzopyran-2-one, benzopyran-4-one), arylalkyl (e.g., benzyl), or arylalkenyl (and R is optionally but preferably substituted one, two or three times with independently selected alkoxy, particularly methoxy, hydroxy, and/or carboxy);

$R_3$ is hydroxy or loweralkoxy, preferably hydroxy or methoxy;

$R_4$ is —C(O)OR" or —NHC(O)OR", where R" is H or loweralkyl, preferably H or methyl;

or a pharmaceutically acceptable salt or prodrug thereof.

Particular examples of group $R^2$ in Formula Ia above include but are not limited to:

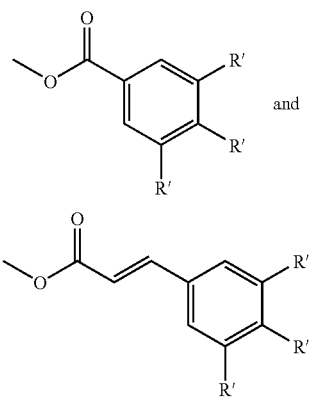

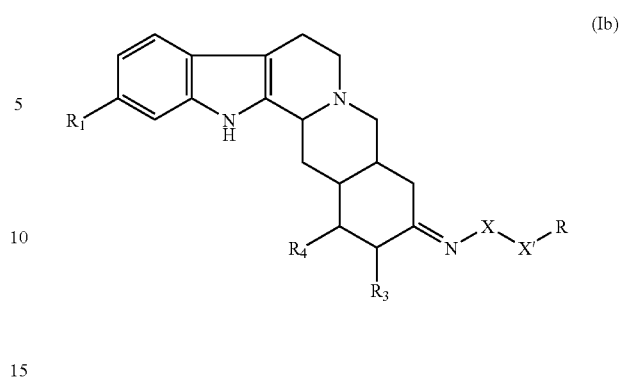

where each R' is independently selected from H, OH, OCH₃, and COOH (and preferably at least one, two or all three of R' are OCH³); or more particularly:

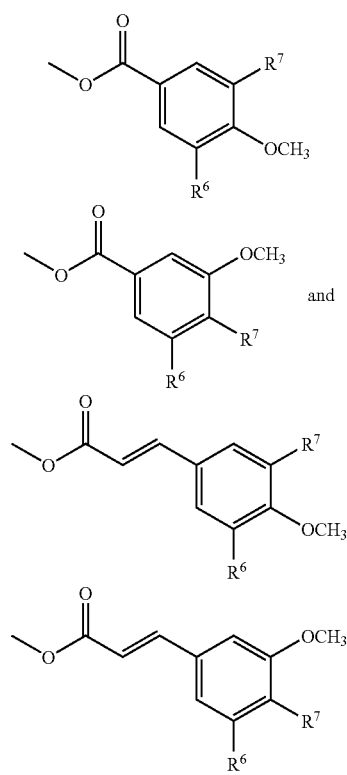

wherein:

R⁶ is H, OH, COOH or alkoxy (preferably alkoxy such as OCH₃)

R⁷ is H, OH, COOH, or alkoxy (preferably alkoxy such as OCH₃).

Additional examples of active compounds of the present invention include compounds of Formula Ib:

wherein:
R₁ is H, loweralkyl, or loweralkoxy, preferably H or methoxy, most preferably methoxy;
X is NH or O;
X' is C(=O) or absent (that is, a covalent bond between X and R);
R₃ is hydroxy or loweralkoxy, preferably hydroxy or methoxy;
R₄ is —C(O)OR" or —NHC(O)OR", where R" is H or loweralkyl, preferably H or methyl; and
R is aryl, arylalkyl (e.g. benzyl), or arylalkenyl (and R is preferably substituted one, two or three times with alkoxy, particularly methoxy);
or a pharmaceutically acceptable salt or prodrug thereof.

Particular examples of group R in Formula Ib above include but are not limited to:

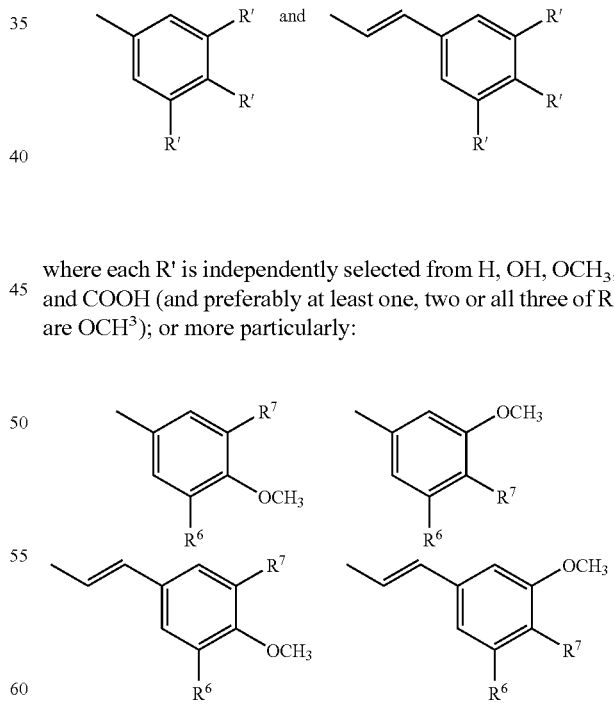

where each R' is independently selected from H, OH, OCH₃, and COOH (and preferably at least one, two or all three of R' are OCH³); or more particularly:

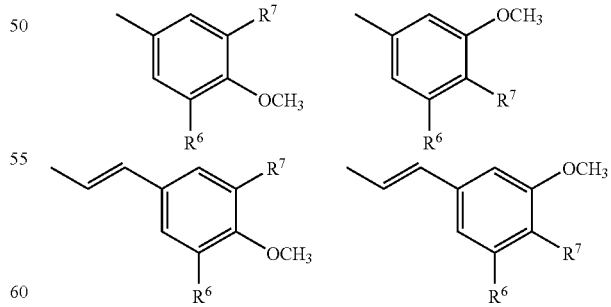

wherein:
R⁶ is H, OH, COOH or alkoxy (preferably alkoxy such as OCH₃)

$R^7$ is H, OH, COOH or alkoxy (preferably alkoxy such as $OCH_3$).

Additional examples of group R in Formula Ia and Ib above include those shown in the corresponding position in U.S. Pat. No. 3,978,065 to Ocelli et al.

Reserpine is known and described in, for example, The Merck Index, Monograph No. 8314 (12$^{th}$ Ed. 1996). In general, reserpine has the structure of Formula II below:

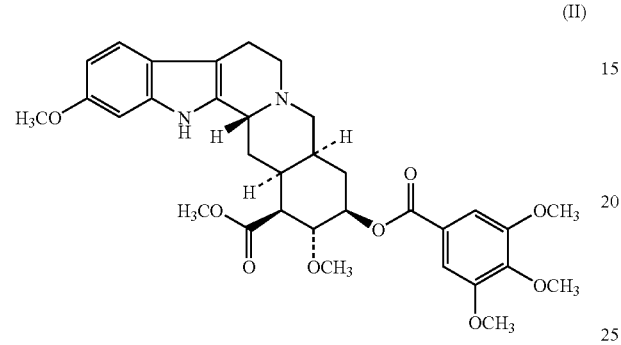
(II)

Yohimbine is known and described in, for example, The Merck Index, Monograph No. 10236 (12$^{th}$ Ed. 1996). In general, yohimbine has the structure of Formula III below:

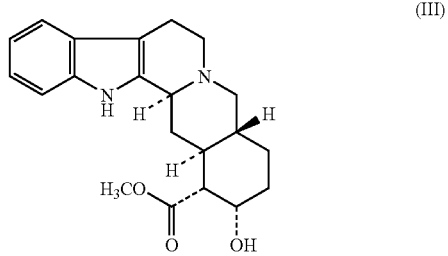 [SMILES: COC(=O)[C@@H]1[C@H]2C[C@H]3c4[nH]c5ccccc5c4CCN3C[C@@H]2CC[C@@H]1O]
(III)

Reserpine analogs are known. Examples include reserpic acid (The Merck Index, Monograph No. 8312 (12$^{th}$ Ed 1996) having the structure of Formula IV below.

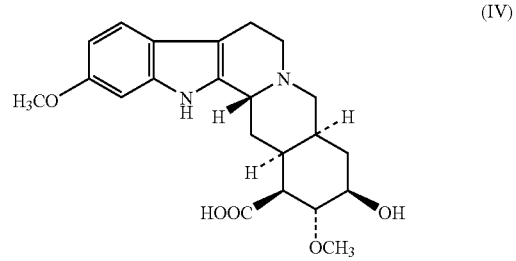 [SMILES: COc1ccc2c3c([nH]c2c1)[C@H]1C[C@H]2[C@H](C[C@@H](O)[C@H](OC)[C@H]2C(=O)O)CN1CC3]
(IV)

Additional examples of reserpine analogs include those described in U.S. Pat. No. 3,978,065 to Occelli et al.

Yohimbine analogs are known. Examples include those described in U.S. Pat. No. 3,940,387 to Saint-Ruf et al.

Additional examples of active compounds include but are not limited to:

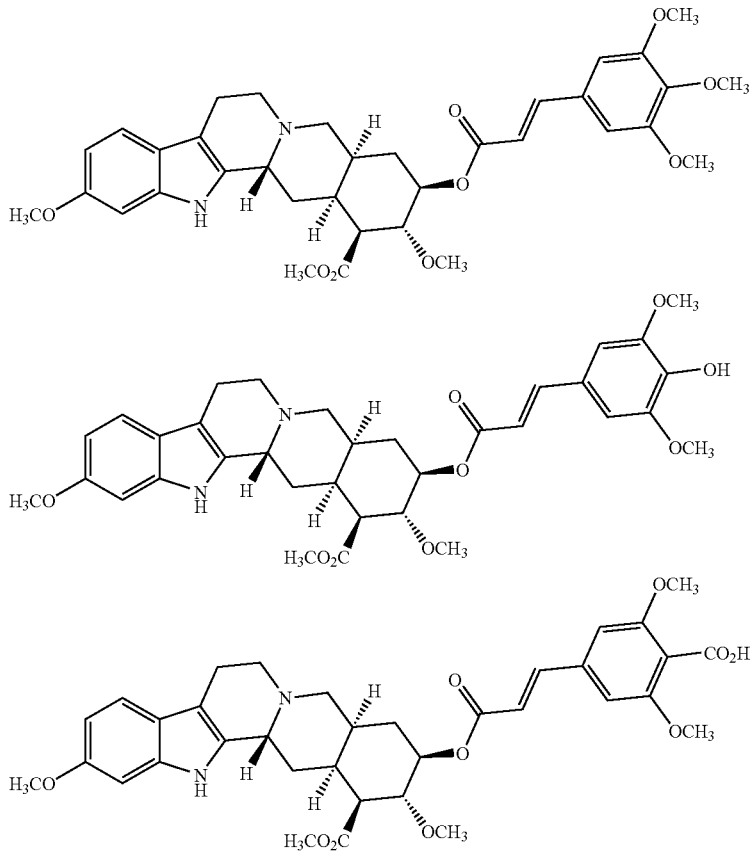

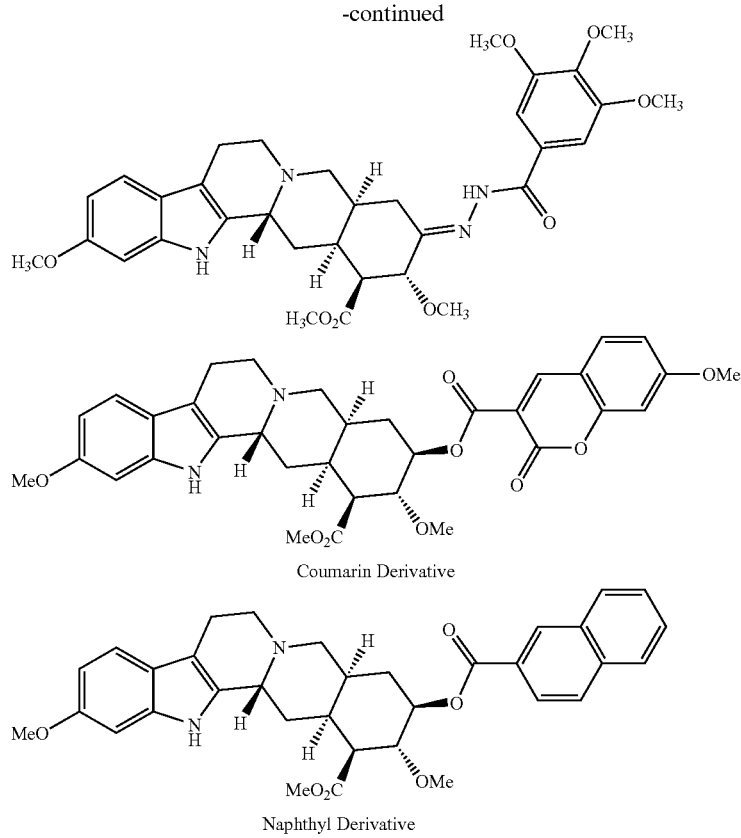

Coumarin Derivative

Naphthyl Derivative and pharmaceutically acceptable salts and prodrugs thereof.

Active compounds can be made according to known techniques, the methods described herein, or variations thereof that will be apparent to those skilled in the art. For example, oxidation of methyl reserpate will provide the corresponding ketone. Condensation of this ketone with various synthetic and commercially available hydrazines will generate the hydrazones.

Active compounds include prodrugs of the foregoing, as noted above. A thorough discussion of prodrugs is provided in T. Higuchi and V. Stella, Prodrugs as Novel Delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. Nos. 6,680,324 and 6,680,322.

The active compounds disclosed herein can, as noted above, be prepared in the form of pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts farmed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations.

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound as described herein, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compounds, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 or 1 to about 20 or 50 mg/kg may be used, with all weights being calculated based upon the weight of the active compound, including the cases where a salt is employed. The frequency and duration of the treatment can be once or twice per day for a period of two to four months or more, or until the condition is essentially controlled.

4. Combination Treatments.

In another embodiment, it is envisioned to use an active compound of the invention in combination with other therapeutic modalities, in like manner as described in U.S. Pat. No. 6,566,395 to Moran. Thus, the active agents described herein may be administered in administered in combination with one or more additional chemotherapeutic agents; and/or in combination with radiation therapy; and/or in combination with ablative or partially ablative surgery. Examples of additional chemotherapeutic agents include but are not limited to the group consisting of androgens, asparaginase, azathioprine, 5-azacitidine, BCG, bleomycin, busulfan, carbetimer, carboplatin chlorambucil, cisplatin, oxaliplatin, corticosteroids, cyclophosphamide, cytarabine, dacarbazine, dactinomycin, daunomycin, doxorubicin, epirubicin, estrogens, etoposide, fadrazole, 5-fluorouracil, gemcitabine, hydroxyurea, ifosfamide, interferon alpha, interferon beta, interferon gamma, an interleukin, isotretinoin, lomustine, melphalan, 6-mercaptopurine, methotrexate, mitomycin-c, mitotane, mitoxantrone, paclitaxel, pentostatin, procabazine, progestins, rituximab, streptozocin, tamoxifen, taxotere, teniposide, thioguanine, thiotepa, topotecan, toremifene, tretinoin, uracil mustard, vinblastine, vincristine and vinorelbine.

The present invention is explained in greater detail in the following non-limiting Examples.

EXAMPLE 1

Cell Biological Analysis of Predicted Compounds

Reserpine was identified as a possible candidate to induce MSH2-dependent cell death by computational modeling and was obtained commercially.

The compound was analyzed in a cell biological setting and their dose-dependent effect on cell survival, in dependence of the MSH2 status, was determined.

Cells proficient and deficient in MSH2 were exposed to increasing concentrations of the drugs and cell survival determined in an MTS assay. This assay is based on the mitochondrial activity of living cells that reduces the tetrazolium product (MTS) into a formazan product that can be spectrophotometrically analyzed at OD490.

Reserpine resulted in reliable data that are shown in FIG. 1. As predicted by computational modeling, a defect in the MMR system (MSH2 deficient) results in a significant increase in resistance to the drug. These data confirm that computational modeling is a useful tool in the prediction of compounds that specifically target the MSH2-dependent cell death pathway.

EXAMPLE 2

Structural and Functional Requirements for Small Molecules to Initiate Mismatch Repair Protein-Dependent Cell Death As noted above, MSH-dependent cell death response can be induced by small molecules that mimic binding to DNA damage and induce cell death in a DNA-independent manner. As the prototype for this induction of MSH2-dependent cell death without genotoxic insult, reserpine, a drug previously in clinical use for hypertension, was identified. The predicted binding of the molecule to the protein was shown to compete with the binding to DNA and induce caspase-dependent cell death.

Here we determine the structural and functional requirements for small molecules to initiate such mismatch repair protein-dependent cell death response. We hypothesized that distinct characteristics and functional groups within a small molecule are required for the correct orientation in the protein binding pocket and the initiation of MSH2-dependent cell death. In a combination of computer-based structural modeling, chemical synthesis and cell biology, we have identified these distinct requirements, which consist of the size of the molecule, the presence of specific functional groups, and its orientation within the protein binding pocket.

Chemical Synthesis.

Methyl reserpate: A suspension of reserpine (1.00 g, 1.64 mmol), NaOMe (0.20 g, 3.61 mmol), and MeOH (50 mL) was refluxed for 4 h (more NaOMe was added twice), cooled, and concentrated to one-third the volume. The solution was diluted with water (60 mL) and acidified to pH=1 with concentrated HCl. The water layer was washed with $Et_2O$ repeatedly and made basic with concentrated $NH_4OH$ and repeatedly extracted with $CH_2Cl_2$ (4×30 mL). The combined organic phases were dried, filtered, and concentrated to give a colorless solid (0.66 g, 97%). $^1H$ NMR ($CDCl_3$) δ 7.85 (s, 1H), 7.32 (d, J=8.4 Hz, 1H), 6.82-6.74 (m, 2H), 4.41 (s, 1H), 3.83 (s, 3H), 3.78 (s, 3H), 3.73-3.68 (m, 1H), 3.59 (s, 3H), 3.58-3.45 (m, 3H), 3.18-3.15 (m, 2H), 3.01-2.91 (m, 2H), 2.68-2.43 (m, 4H), 2.26-2.18 (m, 2H), 1.98-1.75 (m, 4H), 1.27-1.18 (m, 2H); $^{13}C$ NMR ($CDCl_3$) δ 173.5, 156.2, 136.5, 130.9, 122.3, 118.6, 108.99, 108.03, 95.3, 81.6, 75.3, 66.0, 61.1, 58.4, 55.9, 53.8, 51.9, 51.5, 51.3, 49.4, 34.6, 32.9, 32.5, 24.4, 18.5, 16.9, 15.4.

Benzoyl resperine: A solution of methyl reserpate (0.21 g, 0.5 mmol), pyridine (0.79 g, 0.81 mL, 10 mmol), and benzoyl chloride (0.17 mL, 1.5 mmol) was stirred at room temperature for 74 h and concentrated. The residue was taken up in $CHCl_3$ (50 mL) and washed successively with 2% aq. HCl (3×20 mL), 2% aq. NaOH (3×20 mL), water (3×20 mL), and brine. The organic layer was dried, filtered, concentrated, and purified by FC (silica gel, EtOAc, $R_f$=0.53) to give a yellow solid (0.09 g, 33%). $^1H$ NMR ($CDCl_3$) δ 9.19 (s, 1H), 8.09 (d, J=7.2 Hz, 1H), 8.03 (d, J=7.5 Hz, 1H), 7.55 (t, J=7.5 Hz, 1H), 7.49-7.31 (m, 3H), 7.23 (s, 1H), 6.74-6.70 (m, 2H), 5.05-4.96 (m, 1H), 4.84 (s, 1H), 4.10-3.98 (m, 1H), 3.80 (s, 3H), 3.71 (s, 3H), 3.49 (s, 3H), 3.23-3.11 (m, 3H), 2.89-2.84 (m, 1H), 2.75-2.66 (m, 2H), 2.55-2.35 (m, 3H), 2.18-1.97 (m, 5H); $^{13}C$ NMR ($CDCl_3$) δ 172.4, 165.9, 156.6, 137.2, 133.2, 131.6, 130.4, 130.0, 129.7, 128.6, 128.2, 128.0, 121.5, 118.7, 60.9, 55.8, 53.9, 52.1, 51.8, 50.4, 48.2, 33.6, 31.6, 29.8, 29.3, 23.8, 16.3; ESI MS m/z 519 (M+H$^-$).

3-Methoxybenzoyl reserpine: Same as for benzoyl reserpate, using methyl reserpate (0.45 g, 1.08 mmol), pyridine (1.72 g, 1.75 mL, 21.69 mmol), and 3-methoxybenzoyl chloride (0.55 g, 0.44 mL, 3.24 mmol) to give a yellow solid (0.08 g, 13%); $R_f$=0.56 (EtOAc). $^1$H NMR (CDCl$_3$) δ 8.47 (s, 1H), 7.68 (d, J=7.5 Hz, 1H), 7.60 (s, 1H), 7.37 (t, J=7.8 Hz, 1H), 7.29 (d, J=8.7 Hz, 1H), 7.14-7.09 (dd, J=2.1, 8.1 Hz, 1H), 6.84 (s, 1H), 6.77 (dd, J=2.1, 8.7 Hz, 1H), 5.02-4.96 (m, 1H), 4.70 (s, 1H), 3.95 (t, J=9.3 Hz, 1H), 3.87 (s, 3H), 3.85 (s, 3H), 3.84 (s, 3H), 3.52 (s, 3H), 3.20-3.09 (m, 3H), 2.94-2.83 (m, 1H), 2.71-2.64 (m, 2H), 2.48-2.27 (m, 4H), 2.17-1.90 (m, 5H), 1.77-1.50 (m, 1H); $^{13}$C NMR (CDCl$_3$) δ 172.5, 165.8, 159.7, 156.5, 137.1, 131.7, 129.6, 128.3, 122.1, 121.6, 119.6, 118.6, 114.3, 109.4, 106.9, 95.4, 60.9, 55.8, 55.5, 53.6, 52.0, 51.7, 50.3, 48.2, 36.8, 33.5, 31.6, 29.8, 29.2, 24.8, 23.7, 16.2; ESI MS m/z 549 (M+H$^-$).

4-Methoxybenzoyl reserpine: Same as for benzoyl reserpate, using methyl reserpate (0.50 g, 1.21 mmol), pyridine (1.91 g, 1.95 mL, 24.15 mmol), and 4-methoxybenzoyl chloride (0.62 g, 0.50 mL, 3.62 mmol) to give a yellow solid (0.33 g, 50%); $R_f$=0.56 (EtOAc). $^1$H NMR (CDCl$_3$) δ 11.52 (bs, 1H), 9.16 (s, 1H), 7.97 (d, J=8.7 Hz, 2H), 7.17 (d, J=8.1 Hz, 1H), 6.86 (d, J=8.7 Hz, 2H), 6.74 (s, 1H), 6.67 (dd, J=1.8, 8.4 Hz, 1H), 4.95-4.86 (m, 1H), 4.70 (s, 1H), 3.92 (t, J=10.2 Hz, 1H), 3.79 (s, 6H), 3.74 (s, 3H), 3.44 (s, 3H), 3.10-2.98 (m, 3H), 2.81-2.57 (m, 3H), 2.41-2.16 (m, 4H), 2.04-1.85 (m, 5H), 1.61-1.48 (m, 1H); $^{13}$C NMR (CDCl$_3$) δ 176.5, 172.3, 165.7, 163.6, 156.6, 137.2, 131.8, 127.9, 122.8, 121.5, 118.7, 113.8, 109.4, 106.7, 95.3, 60.9, 55.8, 55.5, 53.6, 52.0, 51.6, 50.1, 48.0, 36.8, 36.4, 33.4, 31.4, 29.8, 29.2, 24.8, 23.6, 22.7, 18.5; ESI MS m/z 549 (M+H$^-$).

3,4-Dimethoxybenzoyl reserpine: Same as for benzoyl reserpate, using methyl reserpate (0.50 g, 1.21 mmol), pyridine (1.91 g, 1.95 mL, 24.15 mmol), and 3,4-methoxybenzoyl chloride (0.73 g, 3.62 mmol) to give a yellow solid (0.19 g, 27%); $R_f$=0.31 (EtOAc); $^1$H NMR (CDCl$_3$) δ 10.24 (bs, 1H), 8.72 (s, 1H), 7.71 (dd, J=1.8, 8.4 Hz, 1H), 7.57 (s, 1H), 7.25-7.22 (m, 1H), 6.89 (d, J=8.7 Hz, 1H), 6.80 (s, 1H), 6.74 (dd, J=1.8, 8.4 Hz, 1H), 5.07-4.92 (m, 1H), 4.69 (s, 1H), 3.93 (s, 3H), 3.92 (s, 3H), 3.83 (s, 3H), 3.81 (s, 3H), 3.50 (s, 3H), 3.13-3.06 (m, 3H), 2.68-2.61 (m, 1H), 2.40-2.25 (m, 3H), 2.11-1.87 (m, 5H); $^{13}$C NMR (CDCl$_3$) δ 172.5, 165.7, 156.6, 153.2, 148.8, 137.0, 128.4, 123.7, 122.9, 121.7, 118.7, 112.2, 110.4, 109.4, 107.1, 95.4, 60.8, 56.1, 55.9, 53.6, 52.0, 51.7, 50.3, 48.3, 33.6, 31.7, 29.4, 23.8, 16.3; ESI MS m/z 579 (M+H$^-$).

3,5-Dimethoxybenzoyl reserpine: Same as for benzoyl reserpate, using methyl reserpate (0.50 g, 1.21 mmol), pyridine (1.91 g, 1.95 mL, 24.15 mmol), and 3,5-methoxybenzoyl chloride (0.73 g, 3.62 mmol) to give a yellow solid (0.17 g, 25%); $R_f$=0.53 (EtOAc); $^1$H NMR (CDCl$_3$) δ9.63 (bs, 1H), 8.91 (s, 1H), 7.27-7.18 (m, 2H), 6.80 (s, 1H), 6.74 (dd, J=2.1, 8.4 Hz, 1H), 6.65 (t, J=2.4 Hz, 1H), 5.03-4.93 (m, 1H), 4.76 (s, 1H), 3.93 (t, J=10.2 Hz, 1H), 3.85-3.79 (m, 12H), 3.50 (s, 3H), 3.20-3.05 (m, 3H), 2.90-2.60 (m, 3H), 2.49-2.22 (m, 4H), 2.14-1.90 (m, 5H), 1.69-1.50 (m, 1H); $^{13}$C NMR (CDCl$_3$) δ 176.3, 172.4, 165.7, 160.8, 156.6, 137.2, 132.3, 128.0, 121.6, 118.7, 109.5, 107.4, 106.9, 105.8, 95.4, 60.9, 55.9, 55.7, 53.6, 52.1, 51.6, 50.2, 48.1, 33.5, 31.6, 29.8, 29.2, 23.7, 22.3, 16.2; ESI MS m/z 579 (M+H$^-$).

Cinnamyl reserpine: Same as for benzoyl reserpate, using methyl reserpate (0.50 g, 1.21 mmol), pyridine (1.91 g, 1.95 mL, 24.15 mmol), and cinnamoyl chloride (0.60 g, 3.62 mmol) to give a yellow solid (0.18 g, 27%); $R_f$=0.56 (EtOAc); $^1$H NMR (CDCl$_3$) δ 8.04 (s, 1H), 7.65 (d, J=15.9 Hz, 1H), 7.50-7.45 (m, 2H), 7.36-7.31 (m, 3H), 7.24 (d, J=8.7 Hz, 1H), 6.76-6.74 (m, 1H), 6.69 (dd, J=2.1, 8.4 Hz, 1H), 4.89-4.79 (m, 1H), 4.51 (s, 1H), 3.76 (s, 3H), 3.75 (s, 3H), 3.45 (s, 3H), 3.14-2.77 (m, 4H), 2.63-2.17 (m, 5H), 2.03-1.76 (m, 4H), 1.69-1.40 (m, 1H); $^{13}$C NMR (CDCl$_3$) δ 172.8, 166.4, 156.5, 145.2, 136.8, 134.5, 130.5, 129.6, 129.1, 128.3, 122.0, 118.7, 118.3, 109.3, 107.7, 95.4, 60.9, 55.9, 53.6, 52.0, 51.8, 50.8, 48.7, 33.9, 32.1, 24.8, 24.1, 16.6; ESI MS m/z 545 (M+H$^-$).

3,4-Methylenedioxy benzoyl reserpine: Same as for benzoyl reserpine, using methyl reserpate (0.50 g, 1.21 mmol), pyridine (1.91 g, 1.95 mL, 24.15 mmol), and piperonyloyl chloride (0.67 g, 3.62 mmol) to give a yellow solid (0.31 g, 45%); $R_f$=0.50 (EtOAc); $^1$H NMR (CDCl$_3$ with 2 drops of TFA-d) δ 7.67 (d, J=8.4 Hz, 1H), 7.46-7.37 (m, 2H), 7.26 (s, 1H), 6.89 (d, J=8.1 Hz, 2H), 6.09 (s, 2H), 5.29 (bs, 1H), 5.20-5.09 (m, 1H), 4.04 (t, J=10.5 Hz, 1H), 3.94 (s, 3H), 3.89 (s, 3H), 3.85-3.60 (m, 3H), 3.58 (s, 3H), 3.33 (d, J=12.6 Hz, 1H), 3.20-3.15 (m, 2H), 2.93 (dd, J=3.9, 11.4 Hz, 1H), 2.73-2.60 (m, 1H), 2.39-2.10 (m, 5H); $^{13}$C NMR (CDCl$_3$ with 2 drops of TFA-d) δ 174.1, 153.2, 148.4, 126.6, 120.2, 119.4, 116.4, 112.6, 109.6, 108.9, 108.6, 106.3, 102.4, 78.2, 76.3, 61.4, 56.5, 56.3, 53.4, 50.7, 32.2, 30.6, 28.3, 23.4, 16.0; ESI MS m/z 563 (M+H$^-$).

Cell Viability assays. HEC59 cells and their isogenic counterpart with chromosome 2 transfer were grown in standard growth media of DMEM-F12+10% FBS. Cells were plated in 96 well plates at an appropriate concentration in 100 μl media and incubated overnight. Media was replaced with fresh media containing drug and allowed to incubate for 24 hrs at indicated concentrations. Untreated cells received fresh media containing 0.1% DMSO. One solution reagent (CellTiter 96(r) AQueous One Solution) is added to existing media (20 μl/well) and allowed to incubate 3-4 hrs. A plate reader was used to record the absorbance at 490 nm.

The CellTiter 96® AQueous One Solution Cell Proliferation Assay® is a colorimetric method for determining the number of viable cells in proliferation, cytotoxicity or chemosensitivity assays. The CellTiter 96® AQueous One Solution Reagent contains a tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine ethosulfate; PES). PES has enhanced chemical stability, which allows it to be combined with MTS to form a stable solution. The quantity of formazan product as measured by the amount of 490 nm absorbance is directly proportional to the number of living cells in culture.

Dose-dependent response to nineteen increasing concentrations of the respective compound was determined, and analyzed for IC$_{50}$ values using GraphPad Prism 4™. Each compound was analyzed in triplicates.

Results and Discussion

Small molecule induction of MSH2-dependent cell death. Reserpine initiates MSH2-dependent cell death, independent of genotoxic insult by specifically binding to a "death conformation" of the protein. Based on this observation we hypothesized that distinct functional groups of the compound and a specific binding mode are required for the induction of this cytotoxic response. Rescinnamine is a reserpine derivative that, much like reserpine, functions as an angiotensin-converting enzyme inhibitor that has found clinical applications for hypertension. Its structure differs from reserpine by the length of the hydrophobic bond that connects ring 6 to the remainder of the molecule (Scheme 1).

SCHEME 1

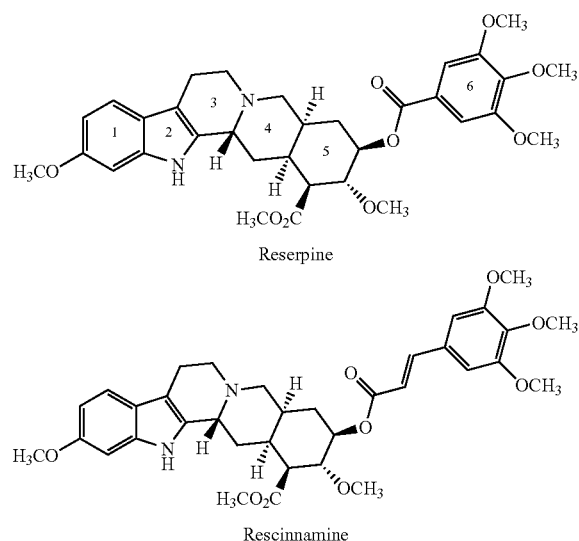

Reserpine

Rescinnamine

Both molecules were modeled into the binding pocket of the MutS protein, and the preferred state was determined by energy minimization. The binding constant ($K_i$) and the partition coefficient as a measure of hydrophobicity were predicted (not shown). Reserpine was predicted to bind to the MutS molecule with a $K_i$ of 67 µM, while rescinnamine had a slightly better binding constant of a predicted 48 µM. Both compounds are suggested to bind in a similar conformation to the protein, with specific protein-compound interactions involving at least two of the methoxy groups of ring 6, the nitrogen atom between rings 3 and 4 and the methoxy group on ring 1. To determine the effect of these compounds on MSH2-dependent cell death, cell viability assays were performed in human cancer cells proficient and deficient for MSH2 after a 24 h exposure to the respective compounds. Results were compared to the response to cisplatin, which was originally used to define the "death conformation" of the proteins. MSH2-dependent cisplatin response is known to be a late response; MSH2-dependent cell death is observed only 48-72 hours after first exposure, which results in a two- to four-fold increase in resistance in MSH2-deficient cells. At 24 hour exposure, only a weak difference between both cell types is observed (Table 1). In contrast, reserpine and rescinnamine induce a robust MSH2-dependent cell death response at 24 hour exposure. Cells deficient in MSH2 show increased resistance to both compounds. The $IC_{50}$ values observed with reserpine demonstrate a 1.5-fold increased resistance in MSH2-deficient cells, which is reminiscent of the effect of long-term exposure to cisplatin (Table 1). Reserpine thus provides a proof-of-principle for the "death conformation" of MSH proteins as a computational target to faithfully identify compounds that induce MSH-dependent cell death. Reserpine shows an MSH2-dependent cell death response that is more rapid than the one observed with cisplatin, suggesting that the cisplatin-induced, MSH2-dependent cell death can be improved. This observation argues against the involvement of DNA damage and the subsequent induction of futile repair cycles. Such a mechanism would require the generation of mismatched DNA as a result of aberrant replication of DNA adducts, a long-term process, as has been suggested for 06-methylguanine.

TABLE 1

$IC_{50}$ values for response of MSH2-deficient and -proficient cells to Reserpine analogs

| Compound | $IC_{50}$ [µM] | | | | Fold differ-ence |
|---|---|---|---|---|---|
| | MSH2-deficient | 95% CL | MSH2-proficient | 95% CL | |
| cisplatin | 75 | 46-130 | 47 | 35-64 | 1.6 |
| reserpine | 93 | 74-120 | 61 | 54-70 | 1.5 |
| rescinnamine | 87 | 53-150 | 39 | 32-47 | 2.6 |
| MJG-6-41 | 110 | 100-120 | 132 | 107-160 | 0.83 |
| 3-methoxy benzoyl | 83 | 74-92 | 88 | 75-104 | 0.94 |
| 4-methoxy benzoyl | 68 | 58-81 | 67 | 59-75 | 1.01 |
| 3,4-dimethoxy benzoyl | 85 | 78-93 | 66 | 59-74 | 1.3 |
| 3,5-dimethoxy benzoyl | 36 | 28-48 | 38 | 30-49 | 0.95 |
| cinnamoyl reserpine | 150 | 92-250 | 130 | 107-160 | 1.2 |
| methylendioxy-benzoyl | 36 | 32-41 | 51 | 45-58 | 0.71 |
| deserpidine | 59 | 51-69 | 48 | 46-51 | 1.2 |

Figure 2:
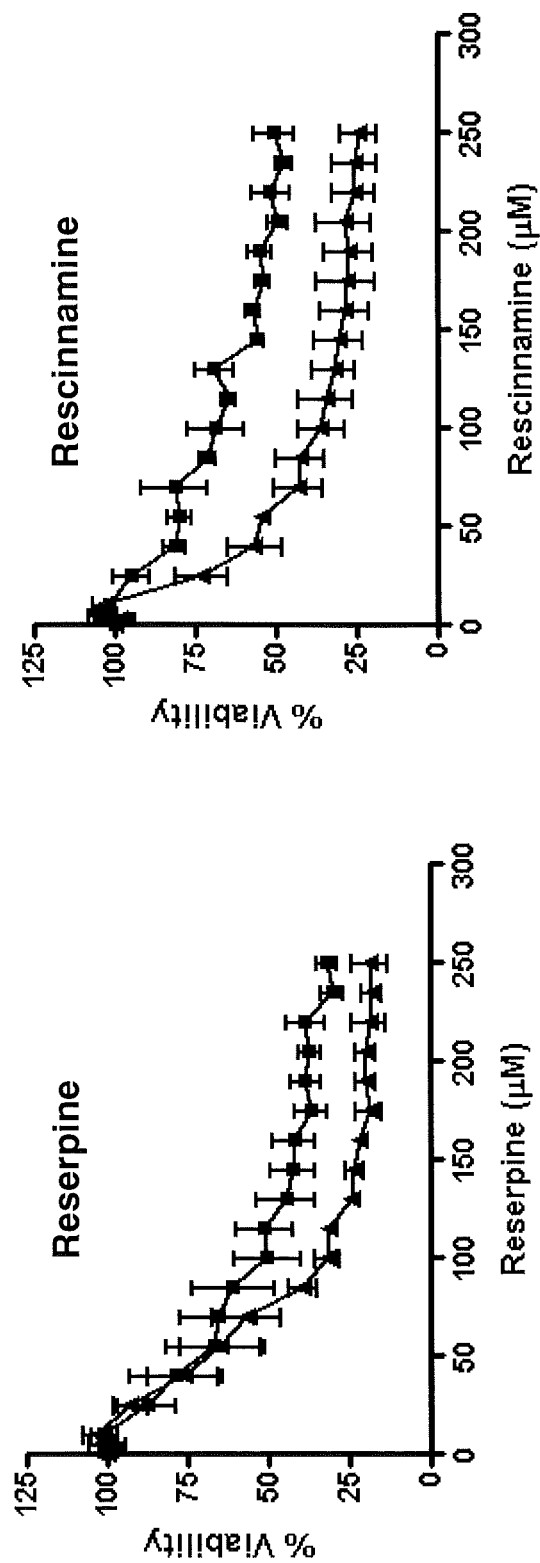
FIG. 2. Results of cell viability assays for MSH2-proficient (triangle) and -deficient (square) cells. Shown are average and standard deviation for independent, triplicate repeats.

Rescinnamine shows MSH2-dependent cell killing at lower concentrations than reserpine (compare $IC_{50}$ of 39 µM to 61 µM) and therewith an improved dependence on functional MSH2, resulting in a roughly 2-fold better MSH2-dependent induction of cell death (FIG. 2; Table 1). Rescinnamine, therewith, shows the best "fast" response with improved MSH2 specificity at a lower concentration. The improved MSH2-dependent cell death observed with rescinnamine is likely due to the increased length of the molecule that would bring essential functional groups closer to their interacting partners within the protein (not shown).

Results from these experiments demonstrate that the predicted "death conformation" of MutS homologous proteins can be used to faithfully identify compounds that induce MSH-dependent cell death, it further substantiates the observation that small molecules can mimic the effects of DNA damage, and it gives credence to the hypothesis that MSH proteins play a more significant role in cell death pathways than originally anticipated.

Alterations in functional groups predict different binding modes to MSH proteins. Based on results obtained with reserpine and rescinnamine, we explored the importance of individual functional groups of the molecules for their interaction with the binding pocket of MutS. In a comparison between reserpine and rescinnamine, several differences in the significance of individual functional groups can be noted. While the methoxy group on ring 1 in reserpine is predicted to be unfavorable for interactions with the protein, it is favorable in the rescinnamine molecule. The ring system 5 shows different polarity in its importance for interactions. While all three methoxy groups on ring 6 are predicted to be important for interactions in reserpine, only two of the three groups are suggested to demonstrate protein interactions for rescinnamine.

Identification of Distinct Requirements for a Small Molecule to Induce MSH2-Dependent Cell Death Based on the predictions of the functionality of individual groups in reserpine and rescinnamine (not shown), their importance for the induction of MSH2-dependent cell death was determined. A number of commercially available reserpine analogs were used as test compounds and straightforward conversion of reserpine to methyl reserpate followed by condensation provided a family of reserpine derivatives (see Materials and Methods). Structural modeling divided the compounds into four subgroups of distinctly different predicted binding modes to MutS:

(1) Reserpine-Like Conformation.

Reserpine and rescinnamine fit into the DNA binding pocket of MutS much like cisplatinated DNA itself (not shown). The space occupied by either molecule largely overlaps with that of DNA. The molecules are stabilized by hydrogen bonds between their methoxy groups and at least three amino acids (G38, R58, R108 of MutS). These residues were previously identified as being important for the interaction with cisplatinated DNA. The phenylalanine (F36) shown to be indispensable for mismatch repair is far removed from the small molecules and shows no significant binding activity. This lack of significance is reminiscent of its failure to exhibit a significant effect on the binding to cisplatinated DNA or, when mutated, on the cytotoxic response to cisplatin. Both molecules show a characteristic bend. Previously, it was suggested that an acquired or pre-existing bend in the ligand for MutS homologous proteins is required for robust binding to their substrates. The existence of such a bend may be a prerequisite for small molecules to specifically bind to MutS homologous proteins and induce a specific response. However, the predicted orientation of the bend in the small molecules appears to be inverted compared to DNA, which may suggest that the actual presence of a bend is not a requirement for cytotoxic response. Reserpine and rescinnamine are the only molecules predicted to preferentially bind in this specific conformation and exhibit the specific interactions with the protein binding pocket.

(2) Flipped conformation. To determine the functional requirements of a small molecule to induce MSH2-dependent cell death, we constructed a number of analogs based on the reserpine structure. We hypothesized, based on the structural predictions, that the methoxy groups on ring #6 will have significant impact on the overall binding to the protein and its binding affinity. We constructed several compounds that either lack all or some of the methoxy groups, resulting in seven different molecules: benzoyl, 3-methoxybenzoyl, 4-methoxybenzoyl, 3,4-dimethoxybenozyl, 3,5-dimethoxybenzoyl, methylendioxybenzoyl and cinnamoyl resperine (Scheme 2).

SCHEME 2

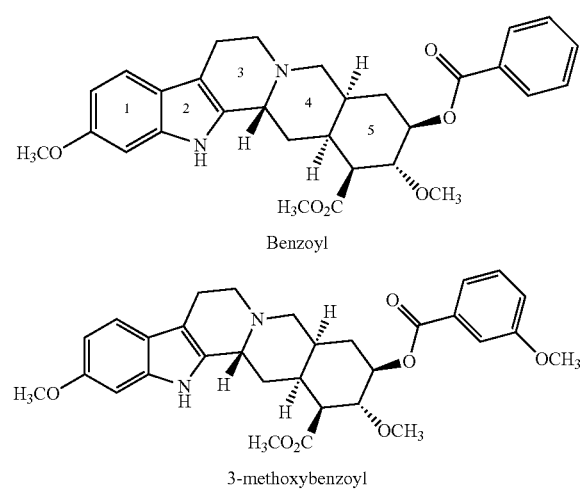

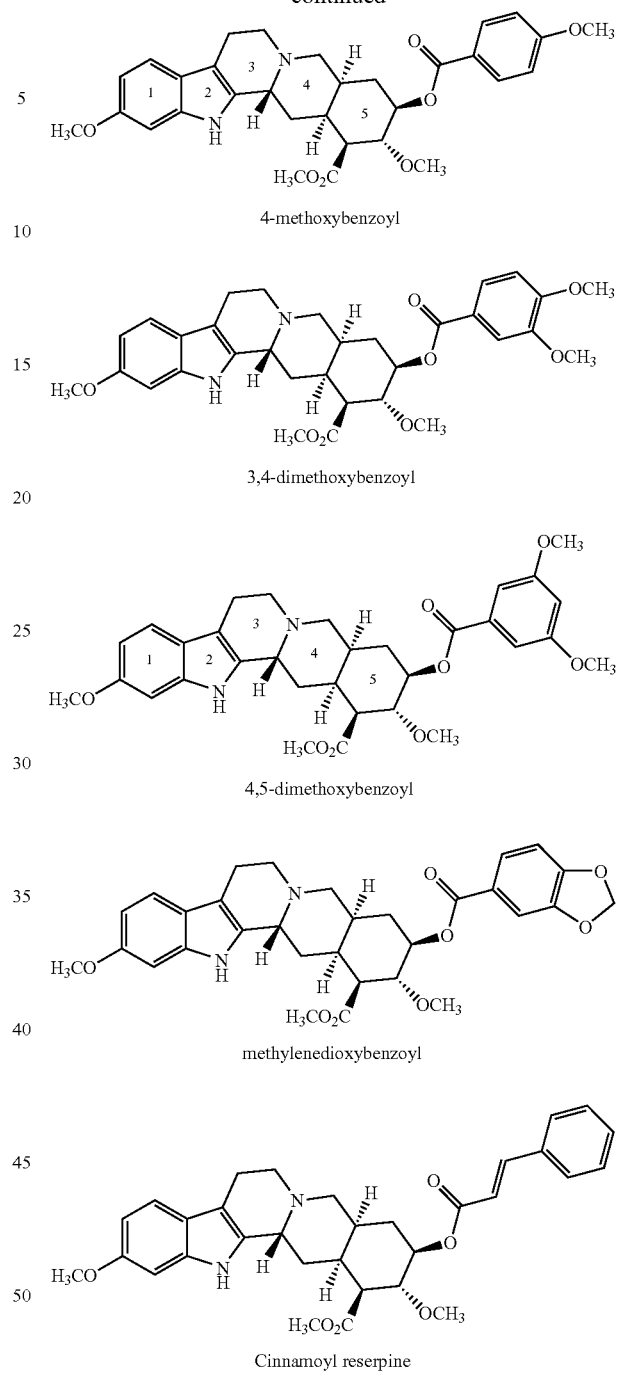

Figure 3A:
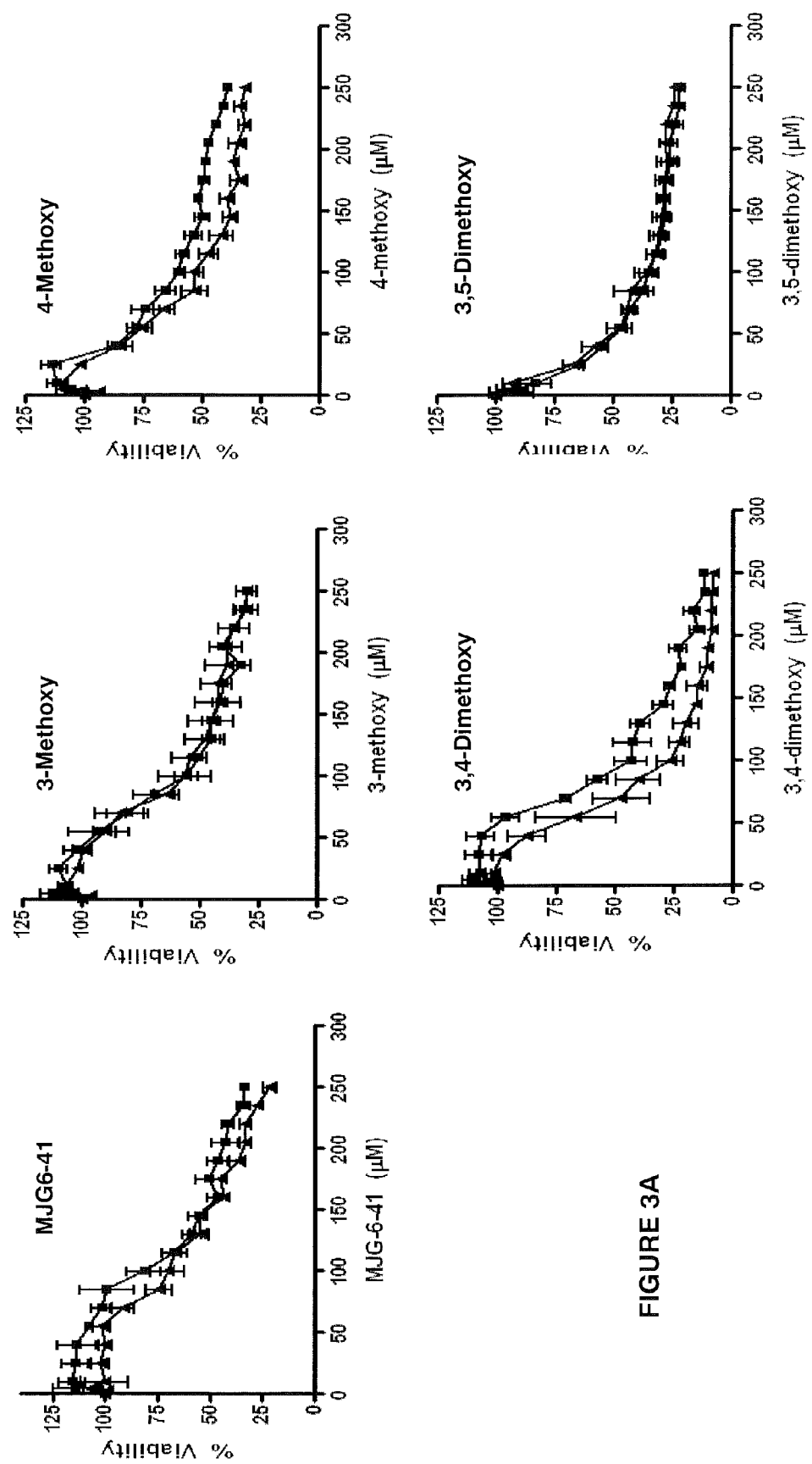
FIG. 3. (a) Cell viability assays of compounds predicted to assume a "flipped conformation" in comparison with reserpine and rescinnamine, in MSH2-proficient (triangle) and -deficient (square) cells. (b) Cell viability assays for deserpidine ("mismatched DNA binding conformation"). (c) Cell viability assays of compounds predicted to assume altered conformations in the MutS binding pocket. Average and standard deviation for independent, triplicate repeats are shown.

Interestingly, the structural predictions suggest a preferred altered binding orientation of these molecules, even for those lacking only one methoxy group (3,4-dimethoxy benzoyl; 3,5-dimethoxy benzoyl). This altered binding mode would flip the molecule and have it oriented the opposite way to the reserpine/rescinnamine. The binding of each one of the five molecules in this orientation is predicted to be strong, with predicted $K_i$ values of 15-32 µM. Determining the cell death response demonstrates the ability of these compounds to induce cell death, however in an MSH2-independent manner (FIG. 3(a), Table 1). The 3,4-dimethoxy benzoyl compound is an exception and the only molecule that initiates a significant MSH2-dependent cell death response. The $IC_{50}$ values for this compound result in 85 µM in MSH2-deficient cells vs. 66 µM in proficient cells, with a 1.3-fold difference, reminiscent of the response observed with reserpine (Table 1). When forced by computational modeling into the "correct" orientation, the predicted binding constant is 93 µM, which would substantiate the cell biology data and suggest a poorer binding to MutS than reserpine. The limitations of the resolution of structural modeling make it impossible to distinguish the binding affinity of this compound from the other methoxy compounds in the "correct" orientation.

Since ring 6 is attached to the remainder of the protein by a rotatable bond, the 3,4-dimethoxy benzoyl compound is indistinguishable from the 4,5-dimethoxy molecule. Whether the presence of two methoxy groups on this ring is sufficient for the induction of MSH2-dependent cell death, or this rotation and the resulting presence of methoxy groups in all three positions enable the appropriate response is unknown.

Methylendioxybenzoyl has an additional ring system on ring 6. This compound is predicted to bind to MutS with a $K_i$ of 19 µM, however, the predicted binding is also found to be in a flipped conformation. The cell death response is opposite to the damage response generally observed in dependence of mismatch repair proteins. MSH2-deficient cells show a higher sensitivity to the compound than proficient ones ($IC_{50}$ of 36 µM in deficient ones, vs. 51 µM in proficient cells, FIG. 3(c), Table 1), reversing the resistance phenotype seen with cisplatin and reserpine/rescinnamine. This result may hint at the involvement of MMR proteins in the elimination of this compound from cells, though further studies are required to substantiate this.

Figure 3B:
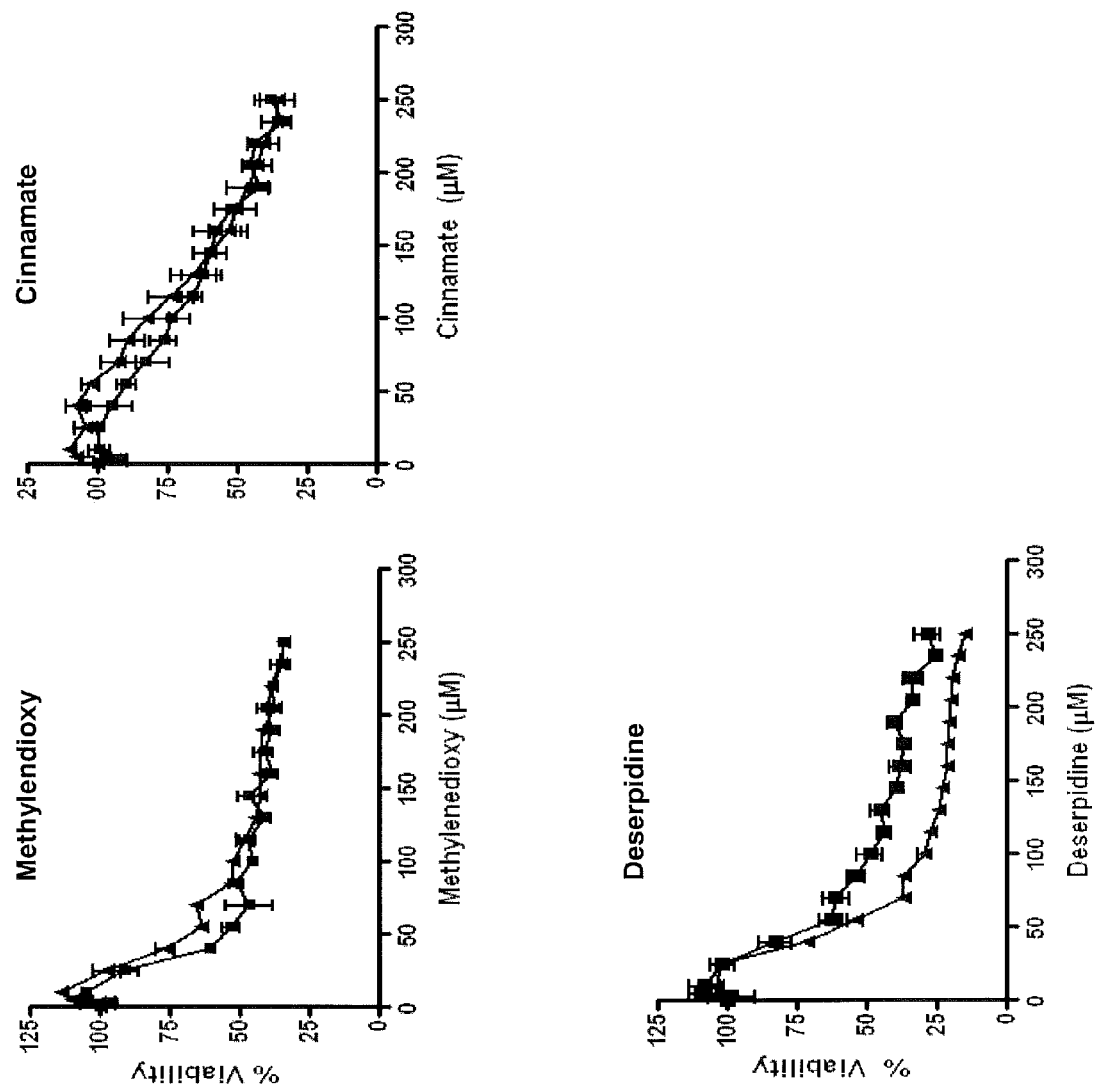
Figure 3C:
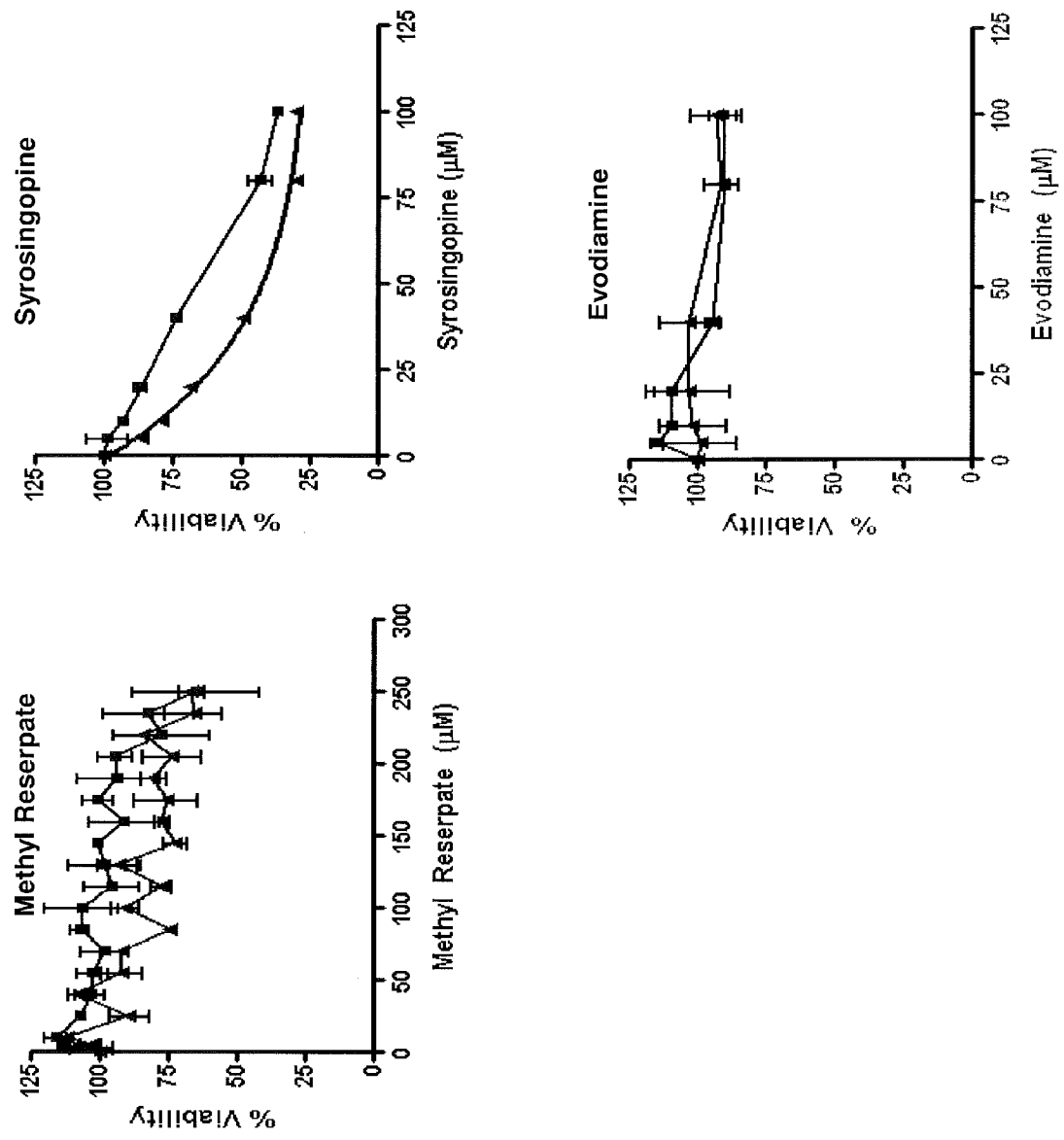

Cinnamoyl reserpine is a Rescinnamate derivative that lacks the methoxy groups on ring 6, similar to the reserpine analog MJG6-41. Again, similar to the corresponding reserpine analog, the predicted binding of Cinnamoyl reserpine to MutS is predicted to occur in the flipped conformation with a binding constant of 14 µM. The compound induces cell death that is independent of functional MSH2 ($IC_{50}$ value of 150 µM in deficient cells vs. 130 µM in proficient cells; FIG. 3(c), Table 1). This result confirms the structural prediction.

Together, these results suggest that in the absence of essential methoxy groups on ring 6 that appear to position the molecules in the correct conformation, a different binding mode is assumed that does not result in MSH2-dependent cell death. This observation suggests that the presence of the methoxy groups is essential for the induction of the MSH "death conformation" and subsequent cytotoxic response.

(3) Mismatch-like binding. The methoxy group on ring 1 was predicted to show unfavorable interactions with the MutS protein for reserpine, but not rescinnamine (not shown). A clinically relevant compound exists that has the general structure of reserpine, but lacks this methoxy group (deserpidine, Scheme 3). Though eliminating a suggestively unfavorable interaction, the predicted binding constant is roughly 2-fold worse than for reserpine (130 µM), which suggests that even an "unfavorable" interaction may be required to correctly orient the molecule in the binding pocket.

SCHEME 3

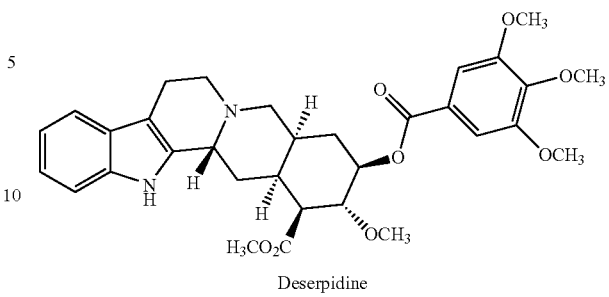

Deserpidine

The predicted binding mode for deserpidine is reminiscent of the binding of mismatched DNA to the protein (not shown). The molecule shows a stronger bending than other compounds and altered orientation that results in the molecule wrapping around the phenylalanine involved in coordinating mismatch binding (F36) (not shown). The predicted specificity for the "death conformation" is reduced for this molecule, which would further confirm the predicted "mismatched DNA"-like binding mode.

The cell biology of this compound revealed cell death induction with no significant specificity for the presence of MSH2 ($IC_{50}$ values of 56 µM in MSH2-deficient vs. 49 µM in -proficient cells; FIG. 3(b), Table 1), confirming the structural predictions. This result suggests that binding in the "mismatched DNA mode" eliminates MSH2-dependent cytotoxic response. It remains to be determined if this compound in particular competes with the repair response of the protein (in preparation).

(4) Non-specific and Altered binding. Some compounds are predicted to bind MutS in an altered conformation. Though binding is still observed in or close to the DNA binding pocket, the general orientation of these compounds is altered when compared to the binding of reserpine/rescinnamine Methyl Reserpate lacks the entire ring 6. This compound is predicted to bind in a distance to the actual binding pocket with a $K_i$ of 101 µM. The molecule only weakly induces cell death in either MSH2-proficient and -deficient cells with no preference for either cell line (FIG. 3(c)). The cell death response was not sufficient to reliably determine $IC_{50}$ values.

Syrosingopine is a commercially available reserpine analog that has found application as an anti-hypertensive drug. Its predicted binding to the mismatch repair protein is the worst among the tested compounds, with a predicted $K_i$ of 1310 µM (Scheme 4).

SCHEME 4

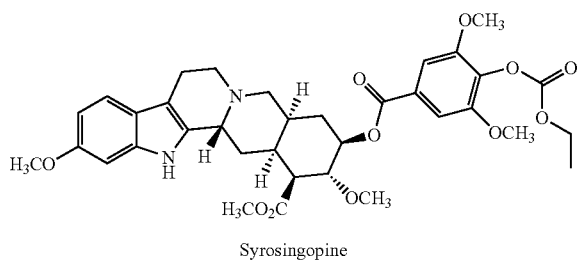

Syrosingopine

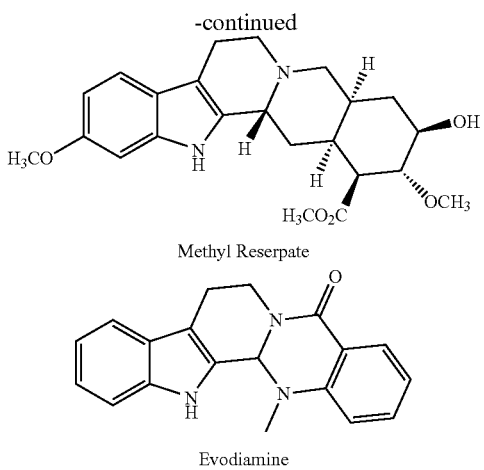

Methyl Reserpate

Evodiamine

This is largely due to the fact that its substitution on position 4 of ring 6 increases its length considerably, which interferes with the binding to the protein (not shown). The binding of the molecule is hence highly "distorted" when compared to the interaction of reserpine/rescinnamine with the protein. Evodiamine, a compound described as aiding in diet-induced obesity, only contains ring systems 1-5 and lacks all methoxy groups seen in reserpine/rescinnamine. This compound shows no specific binding in the computational docking experiments, and hence does not result in a predictable binding constant. In the cell system, this molecule shows no significant cytotoxic effect, in either the presence or absence of MSH2 (FIG. 3(c)). This is presumably due to the fact that evodiamine cannot establish any of the required interactions with the MMR protein.

We here determined the structural and functional requirements for a small molecule to induce this specific cell death pathway. We were able to demonstrate that highly specific features are required for a molecule, which include the overall size, the presence of certain functional groups and orientation of the molecule within the protein.

Figure 4:
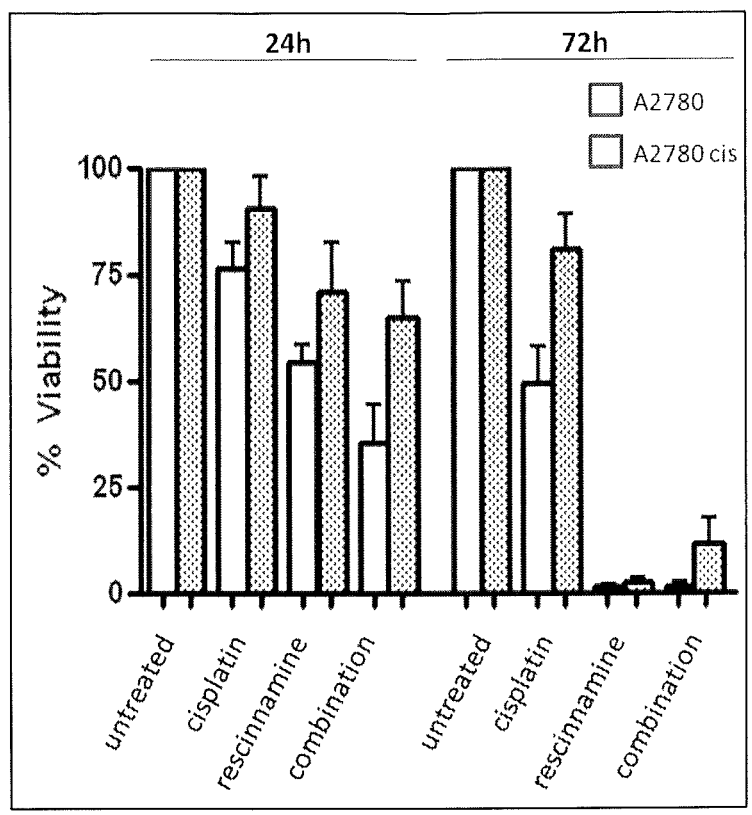
FIG. 4: Results of MTS assay demonstrating cell killing after exposure to indicated drugs for indicated time frames (10 uM cisplatin, 20 uM rescinnamine). A2780 is a cisplatinum-sensitive ovarian cancer cell line, A2780 its isogenic, but cisplatinum-resistant counterpart. Shown are average and standard deviations of a minimum of 3 individual experiments. Results were normalized to the untreated control.

Additional data. As noted above, we have used computational modeling to identify compounds that mimic cisplatinum in its ability to induce cell death in cancer cells. Molecules identified by this method overcome platinum resistance in ovarian cancer cells. The identified compound, rescinnamine, belongs in the group of Rauwolfia alkaloids, previously in clinical use for hypertension. We determined that this compound indeed induces the targeted, MSH2/6-dependent cell death in a caspase-3-dependent cell death asay that simulates the action of cisplatinum. Based on its ability to mimic cisplatinum cell death, the induction of this apoptotic pathway is capable of overcoming cisplatinum resistance in ovarian cancer cells. The induced cell killing is dramatic, and not reversed by combination treatment with cisplatinum (FIG. 4). In addition, rescinnamine proved to be more effective in sensitive ovarian cancer cells than cisplatinum at the indicated concentrations and duration of exposure (FIG. 4).

Figure 5:
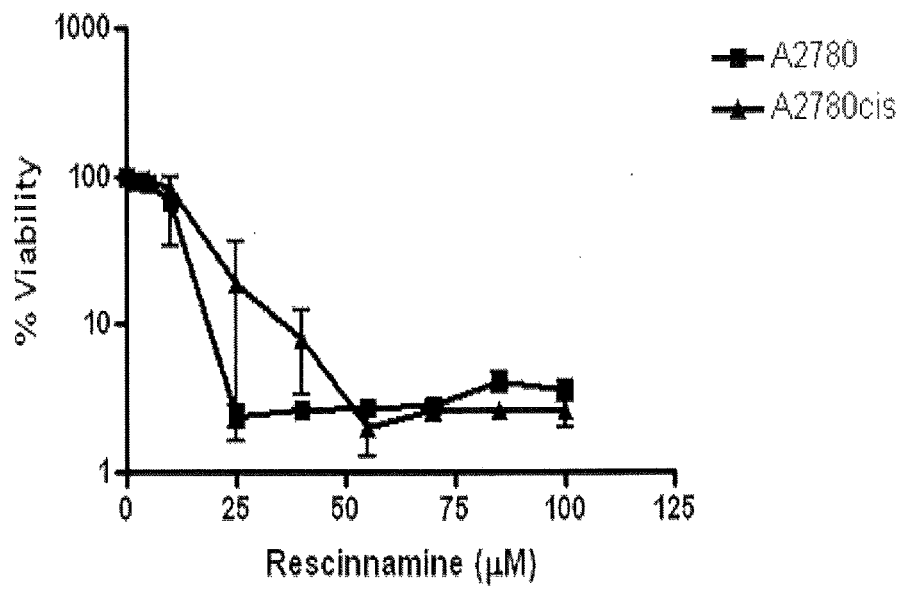
FIG. 5: MTS assays of platinum sensitive (A2780) and resistant (A2780cis) cells in the presence of 10 uM cisplatinum and increasing concentrations of rescinnamine.

We next determined if rescinnamine increases the sensitivity to cisplatinum, or overcomes resistance by inducing the cisplatinum-like cell death (as was predicted). Shown in FIG. 5 is treatment of sensitive and resistant ovarian cancer cells with fixed concentrations of cisplatinum and increasing concentrations of rescinnamine. Increasing concentrations of rescinnamine show concentration-dependent, significant cell death in both sensitive and resistant cells (FIG. 5), while increasing concentrations of cisplatinum in the presence of rescinnamine show a much less pronounced cell death (data not shown). If rescinnamine sensitizes cells to cisplatinum, treatment with increasing cisplatinum in the presence of rescinnamine should induce significant cell death in resistant cells. This is not observed (data not shown), indicating that cisplatinum remains to be ineffective and rescinnamine replaces its function.

These data suggest that the computational and targeted identification of compounds that induce a cell death system that mimics cisplatinum activity can overcome cisplatinum resistance in ovarian cancer cells.

Figure 6:
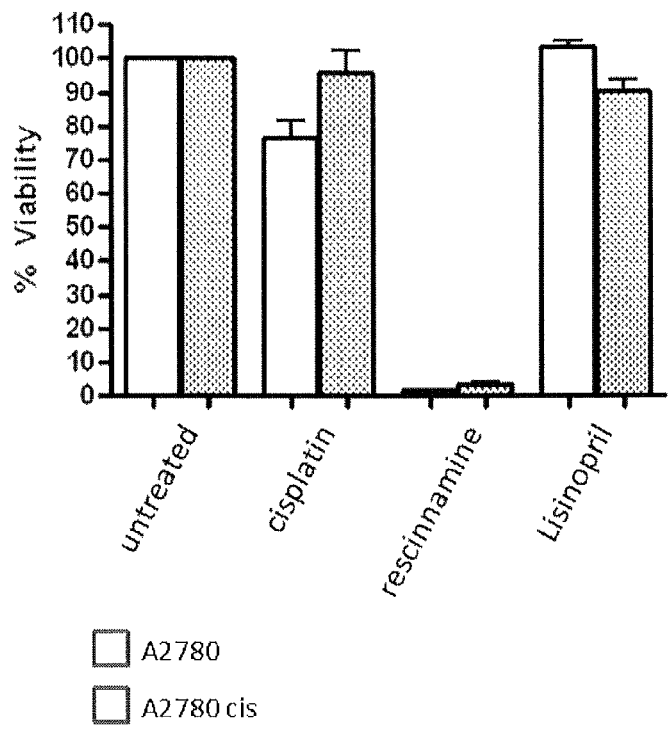
FIG. 6: MTS assay of A2780 and A2780cis ovarian cancer cells, untreated, treated with 10 uM cisplatin, 20 uM rescinnamine and lisinopril.

The cell killing activity of rescinnamine is not dependent on its ACE inhibitor function, since the addition of another ACE inhibitor (lisinopril) does not show the same effect (FIG. 6).

Figure 7:
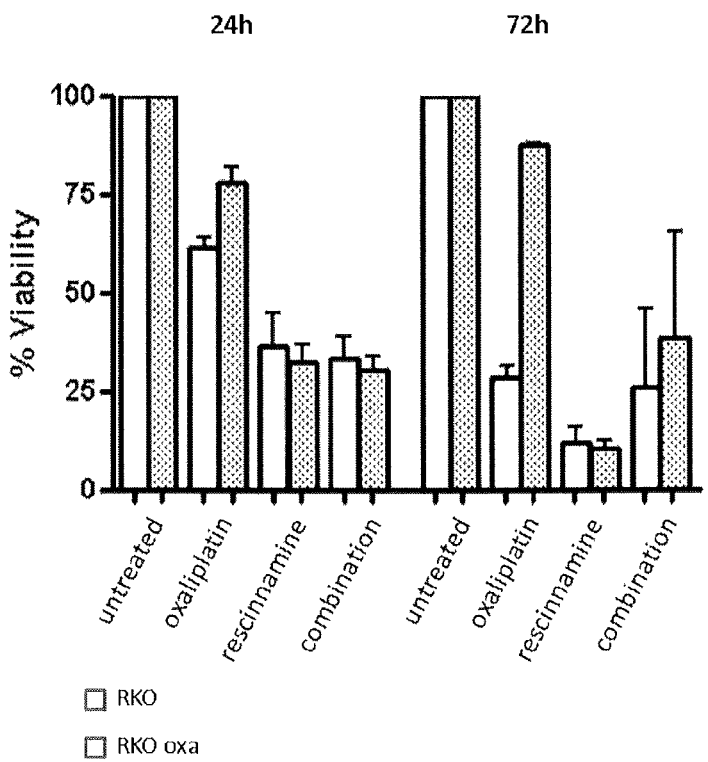
FIG. 7: MTS assay of colorectal cancer cells sensitive (RKO) and insensitive (RKO oxa) to oxaliplatin, treated with oxaliplatin, rescinnamine and combination.

Current treatment of colorectal cancer includes oxaliplatin. Despite success with chemotherapeutic intervention, patients show resistance to this platinum derivative. We next analyzed if rescinnamine would overcome oxaliplatin in colorectal cancer cells (FIG. 7). We demonstrate that rescinnamine overcomes oxaliplatin resistance, albeit not to the same extent as cisplatinum resistance.

The foregoing is illustrative of the present invention, and is not to be construed as limiting thereof. The invention is defined by the following claims, with equivalents of the claims to be included therein.

What is claimed is:
1. A compound of Formula Ia:

(Ia)

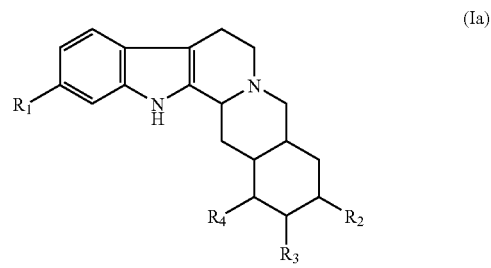

wherein:
  $R_1$ is methoxy;
  $R_2$ is:

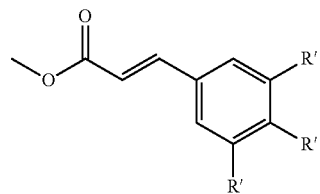

where each R' is independently selected from H, OH, $OCH_3$, and COOH, subject to the proviso that at least one R' is COOH;
  $R_3$ is hydroxy or loweralkoxy,
  $R_4$ is —C(O)OR' or —NHC(O)OR', where R' is H or loweralkyl;
or a pharmaceutically acceptable salt or ester thereof.

2. A composition comprising a compound of claim 1 in a pharmaceutically acceptable carrier.

3. The composition of claim 2, further comprising at least one additional chemotherapeutic agent.

4. The composition of claim 3, wherein said additional chemotherapeutic agent is selected from the group consisting of androgens, asparaginase, azathioprine, 5-azacitidine, BCG, bleomycin, busulfan, carbetimer, carboplatin chlorambucil, cisplatin, oxaliplatin, corticosteroids, cyclophosphamide, cytarabine, dacarbazine, dactinomicin, daunomycin, doxorubicin, epirubicin, estrogens, etoposide, fadrazole, 5-flurouracil, gemcitabine, hydroxyurea, ifosfamide, interferon alpha, interferon beta, interferon gamma, an interleukin, isotretinoin, lomustine, melphalan, 6-mercaptopurine, methotrexate, mitomycin-c, mitotane, mitoxantrone, paclitaxel, pentostatin, procabazine, progestins, rituximab, streptozocin, tamoxifen, taxotere, teniposide, thioguanine, thiotepa, topotecan, toremifene, tretinoin, uracil mustard, vinblastine, vincristine and vinorelbine.

5. The compound of claim 1 selected from the group consisting of:

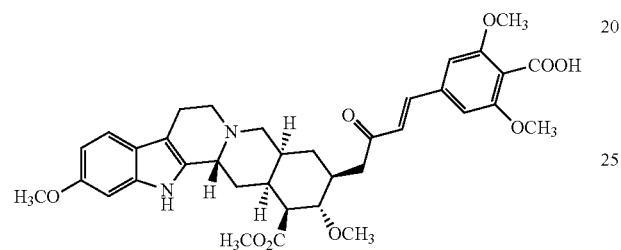

and pharmaceutically acceptable salts thereof.

* * * * *